United States Patent
Miyake et al.

(10) Patent No.: US 10,442,752 B2
(45) Date of Patent: Oct. 15, 2019

(54) METHOD FOR PREPARING (7E)-7, 9-DECADIENOATE ESTER

(71) Applicant: SHIN-ETSU CHEMICAL CO., LTD., Tokyo (JP)

(72) Inventors: Yuki Miyake, Joetsu (JP); Takeshi Kinsho, Joetsu (JP); Ryo Komatsu, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 16/142,529

(22) Filed: Sep. 26, 2018

(65) Prior Publication Data

US 2019/0106374 A1  Apr. 11, 2019

(30) Foreign Application Priority Data

Oct. 6, 2017 (JP) .................. 2017-195641

(51) Int. Cl.

| | | |
|---|---|---|
| *C07C 67/327* | (2006.01) | |
| *C07C 67/24* | (2006.01) | |
| *C07C 69/734* | (2006.01) | |
| *C07C 67/03* | (2006.01) | |
| *C07C 67/303* | (2006.01) | |
| *C07C 67/313* | (2006.01) | |
| *C07C 67/32* | (2006.01) | |
| *C07C 67/343* | (2006.01) | |

(52) U.S. Cl.
CPC .......... *C07C 67/327* (2013.01); *C07C 67/03* (2013.01); *C07C 67/24* (2013.01); *C07C 67/303* (2013.01); *C07C 67/313* (2013.01); *C07C 67/32* (2013.01); *C07C 67/343* (2013.01); *C07C 69/734* (2013.01); *C07B 2200/09* (2013.01)

(58) Field of Classification Search
CPC ........ C07C 67/327; C07C 67/03; C07C 67/24
USPC ....................................................... 560/183
See application file for complete search history.

(56) References Cited

FOREIGN PATENT DOCUMENTS

EP    2 789 602 A1    10/2014

OTHER PUBLICATIONS

Siderhurst et al.; "Disruption of Darna pallivitta (Lepidoptera: Limacodidae) by Conventional and Mobile Pheromone Deployment" 2015; J. Insect. Science 15(1): 1-8.
Siderhurst et al.; "n-Butyl (E)-7,9-decadienoate: sex pheromone component of the nettle caterpillar, Darna pallivitta;" 2007; Entomol. Exp. Appl. 125: 63-69.
Sasaerila et al.; "Decadienoates: Sex Pheromone Components of Nettle Caterpillars Darna trima and D. bradleyi;" 2000; J. Chem. Ecol. 26(8): 1969-1981.
Feb. 12, 2019 extended Search Report issued in European Patent Application No. 18198311.5.
Bestmann et al. "Pheromone XXXVI. Synthese konjugiert-ungesättigter Lepidopterenpheromone und Analoga". Liebigs Ann. Chem., 1981, 2117-2138.

*Primary Examiner* — Deborah D Carr
(74) *Attorney, Agent, or Firm* — Oliff PLC

(57) ABSTRACT

One object of the invention is to provide a method for preparing a 9,9-dialkoxy-7-nonynoate ester and (7E)-7,9-decadienoate ester, which are valuable as intermediates. The method for preparing a (7E)-7,9-decadienoate ester (5) comprises at least steps of: hydrolyzing a 9,9-dialkoxy-7-nonenoate ester (2), $R^3O(R^2O)CHCH=CH(CH_2)_5CO_2R^1$, to form a (7E)-9-oxo-7-nonenoate ester (3); and subjecting the (7E)-9-oxo-7-nonenoate ester (3) to a Wittig reaction with a triarylphosphonium methylide (4), $Ar_3P=CH_2$, to form the (7E)-7,9-decadienoate ester (5). The 9,9-dialkoxy-7-nonenoate ester may be prepared by, for example, reducing a 9,9-dialkoxy-7-nonynoate ester (1).

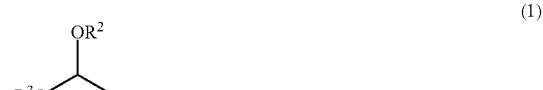

(1)

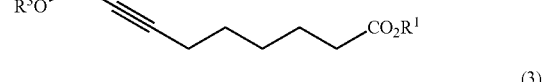

(3)

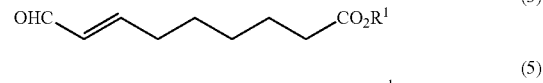

(5)

8 Claims, No Drawings

METHOD FOR PREPARING (7E)-7, 9-DECADIENOATE ESTER

TECHNICAL FIELD

The present invention relates to a method for preparing a (7E)-7,9-decadienoate ester.

BACKGROUND ART

Nettle caterpillars such as *Darna pallivitta, Darna trima* and *Darna bradleyi* are major pests that attack palms in Southeast Asia and Hawaii. They feed on leaves of palms and eventually kill the trees, leading to a decreased crop. Therefore, biological pest controls have been attracting great interest, promising one of which is the use of a sex pheromone (Non-Patent Literature 1).

Sex pheromone compositions of Nettle caterpillars differ among species. It was confirmed that several species have an alkyl (7E)-7,9-decadienoate and an alkenyl (7E)-7,9-decadienoate (hereinafter collectively referred to as "(7E)-7,9-decadienoate ester") as a component in sex pheromone compositions (Non-Patent Literatures 1, 2 and 3).

With regard to a method for producing these sex pheromones of the Nettle caterpillar, there is a report that methyl (7E)-7,9-decadienoate, ethyl (7E)-7,9-decadienoate and butyl (7E)-7,9-decadienoate, which are sex pheromones of *Darna pallivitta*, can be prepared by a method comprising alkylation of 3-sulfolene, desulfurization, deprotection of THP, oxidation of the alcohol with pyridinium dichromate (PDC) and condensation using N, N'-dicyclohexylcarbodiimide (DCC) (Non-Patent Literature 2). It is also reported that 2-methylbutyl (7E)-7,9-decadienoate and (2E)-2-hexenyl (7E)-7,9-decadienoate, i.e., sex pheromones of *Darna trima*, and methyl (7E)-7,9-decadienoate and 2-methylpropyl (7E)-7,9-decadienoate, i.e., sex pheromones of *Darna bradleyi*, can be prepared in a similar method (Non-Patent Literature 3).

LIST OF PRIOR ART

Non-Patent Literature

[Non-Patent Literature 1] M. S. Siderhurst et al., "Disruption of *Darna pallivitta* (Lepidoptera: Limacodidae) by Conventional and Mobile Pheromone Deployment" 2015, J. Insect. Science 15(1): 1-8.

[Non-Patent Literature 2] M. S. Siderhurst et al., "n-Butyl (E)7,9-decadienoate: sex pheromone component of the nettle caterpillar, *Darna pallivitta*", 2007, Entomol. Exp. Appl. 125: 63-69.

[Non-Patent Literature 3] Y. Sasaerila et al., "Decadienoates: Sex Pheromone Components of Nettle Caterpillars *Darna trima* and *D. bradleyi*", 2000, J. Chem. Ecol. 26(8): 1969-1981.

SUMMARY OF THE INVENTION

The both methods reported in Non-Patent Literatures 2 and 3 involve alkylation of 3-sulfolene as a key reaction. However, hexamethylphosphoric triamide is used as a solvent, which is carcinogenic. Therefore, the methods are unsuitable for industrial production.

In addition, the methods reported in Non-Patent Literatures 2 and 3 involve reactions such as desulfurization and PDC oxidation which impose heavy environmental burdens. The oxidation is accompanied with a substantial risk of explosion. These issues also make it difficult to implement these methods in an industrial scale. A further problem is a low geometrical selectivity as evidenced by E/Z=96/4 at the 7-position.

In view of the above, one of the objects of the present invention is to provide a method for preparing (7E)-7,9-decadienoate ester.

Through extensive research, the present inventors have found that a (7E)-7,9-decadienoate ester can be prepared in a good yield and an enhanced geometrical purity by the use of a 9,9-dialkoxy-7-nonynoate ester which is, in a preferable embodiment, derived from a 9,9-dialkoxy-7-nonenoate ester.

According to one aspect of the present invention, there is provided a method for preparing a (7E)-7,9-decadienoate ester of the general formula (5):

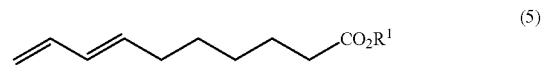
(5)

wherein $R^1$ is a monovalent hydrocarbon group having 1-15 carbon atoms, the method comprising at least steps of:

hydrolyzing a 9,9-dialkoxy-7-nonenoate ester of the general formula (2):

$$R^3O(R^2O)CHCH=CH(CH_2)_5CO_2R^1 \quad (2)$$

wherein $R^1$ is as defined above, and $R^2$ and $R^3$ are each independently a monovalent hydrocarbon group having 1-15 carbon atoms or together form a divalent hydrocarbon group having 2-10 carbon atoms, $R^2$-$R^3$,
to form a (7E)-9-oxo-7-nonenoate ester of the general formula (3):

(3)

wherein $R^1$ is as defined above; and subjecting the (7E)-9-oxo-7-nonenoate ester (3) to a Wittig reaction with a triarylphosphonium methylide of the general formula (4):

$$Ar_3P=CH_2 \quad (4)$$

wherein Ar is an aryl group having 6 or 7 carbon atoms, to form the (7E)-7,9-decadienoate ester.

According to a preferable embodiment, the method for preparing the (7E)-7,9-decadienoate ester further comprises a step of:

reducing a 9,9-dialkoxy-7-nonynoate ester of the general formula (1):

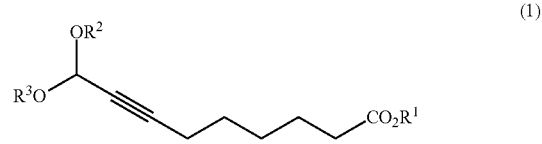
(1)

wherein $R^1$, $R^2$ and $R^3$ are as defined above,
to form the 9,9-dialkoxy-7-nonenoate ester of the general formula (2).

According to another aspect of the present invention, there is provided a method for preparing a 9,9-dialkoxy-7-nonynoate ester of the general formula (1):

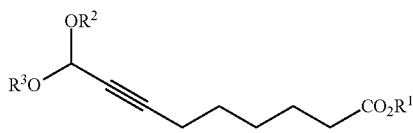

wherein $R^1$ is a monovalent hydrocarbon group having 1-15 carbon atoms, and $R^2$ and $R^3$ are each independently a monovalent hydrocarbon group having 1-15 carbon atoms or together form a divalent hydrocarbon group having 2-10 carbon atoms, $R^2$-$R^3$, the method comprising at least steps of:

alkylating a 7-halo-1,1-dialkoxy-2-heptyne of the general formula (7):

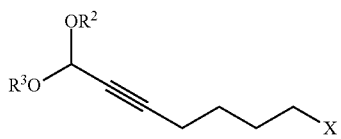

wherein $R^2$ and $R^3$ are as defined above, and X is a halogen atom, with a malonate diester of the general formula (8):

wherein $R^1$ is as defined above,
to form a 7,7-dialkoxy-5-heptynyl malonate diester of the general formula (9):

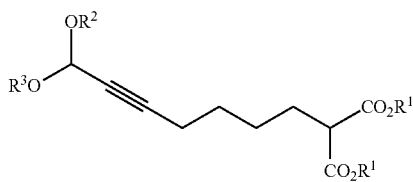

wherein $R^1$, $R^2$ and $R^3$ are as defined above; and
subjecting the 7,7-dialkoxy-5-heptynyl malonate diester (9) to a Krapcho reaction to form the 9,9-dialkoxy-7-nonynoate ester (1).

According to another aspect of the present invention, there is provided a 9,9-dialkoxy-7-nonynoate ester of the general formula (1):

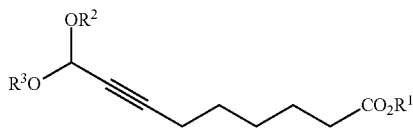

wherein $R^1$ is a monovalent hydrocarbon group having 1-15 carbon atoms, and $R^2$ and $R^3$ are each independently a monovalent hydrocarbon group having 1-15 carbon atoms or together form a divalent hydrocarbon group having 2-10 carbon atoms, $R^2$-$R^3$.

According to the invention, (7E)-7,9-decadienoate ester can be prepared in a good yield and an enhanced geometrical purity, without relying on an oxidation reaction. It is also possible to produce a (7E)-7,9-decadienoate ester in a convergent manner, regardless whether the 9,9-dialkoxy-7-nonenoate ester is an E- or Z-isomer or a mixture thereof. The present invention also realizes the production of comprehensive (7E)-7,9-decadienoate esters, which are sex pheromones of the Nettle caterpillar. 9,9-Dialkoxy-7-nonynoate esters are useful for the production of 9,9-dialkoxy-7-nonenoate esters.

DESCRIPTION OF EMBODIMENTS

First, the 9,9-dialkoxy-7-nonynoate ester of the general formula (1) will be described in more detail. In the general formula (1), $R^1$ is a monovalent hydrocarbon group having 1-15 carbon atoms, and $R^2$ and $R^3$ are each independently a monovalent hydrocarbon group having 1-15 carbon atoms or together form a divalent hydrocarbon group having 2-10 carbon atoms, $R^2$-$R^3$.

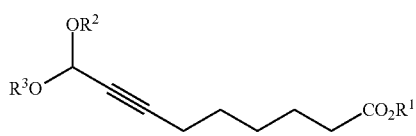

In the 9,9-dialkoxy-7-nonynoate ester of the general formula (1), $R^1$ is a monovalent hydrocarbon group having 1-15 carbon atoms. The monovalent hydrocarbon group $R^1$ has 1-15, more preferably 1-10, still more preferably 1-6 carbon atoms.

Non-limiting examples of the monovalent hydrocarbon group $R^1$ include linear alkyl groups, such as methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, and n-pentadecyl groups; branched alkyl groups, such as 1-methylethyl, 2-methylpropyl, 2-methylbutyl, 2-methylpentyl, 2-methylhexyl, 3-methylbutyl, 3-methylpentyl, 3-methylhexyl, 4-methylpentyl, and 4-methylhexyl groups; linear 1-alkenyl groups, such as 1-ethenyl, (1E)-1-propenyl, (1Z)-1-propenyl, (1E)-1-butenyl, and (1Z)-1-butenyl groups; branched 1-alkenyl groups, such as 1-methylethenyl group; linear 2-alkenyl groups, such as 2-propenyl, (2E)-2-butenyl, (2Z)-2-butenyl, (2E)-2-pentenyl, (2Z)-2-pentenyl, (2E)-2-hexenyl, and (2Z)-2-hexenyl groups; branched 2-alkenyl groups, such as 2-methyl-2-propenyl group; linear 3-alkenyl groups, such as 3-butenyl, (3E)-3-pentenyl, (3Z)-3-pentenyl, (3E)-3-hexenyl, and (3Z)-3-hexenyl groups; branched 3-alkenyl groups, such as 3-methyl-3-butenyl group; linear alkynyl groups, such as 1-propynyl, 3-butynyl, and 1-heptynyl groups; and cycloalkyl groups, such as cyclopropyl, 2-methylcyclopropyl, cyclobutyl, cyclopentyl, and cyclohexyl groups; and isomers thereof. A part of the hydrogen atoms in these hydrocarbon groups may be substituted with, e.g., a methyl or ethyl group.

As the monovalent hydrocarbon group $R^1$, methyl, ethyl, n-butyl, 2-methylpropyl, 2-methylbutyl and (2E)-2-hexenyl groups are preferable in view of the handling and for the production of the sex pheromone.

In the general formula (1), $R^2$ and $R^3$ are each independently a monovalent hydrocarbon group having 1-15 carbon atoms or together form a divalent hydrocarbon group having 2-10 carbon atoms, $R^2$-$R^3$. Each of the monovalent hydrocarbon groups $R^2$ and $R^3$ preferably has 1-6 carbon atoms.

Non-limiting examples of the monovalent hydrocarbon groups $R^2$ and $R^3$ include linear saturated hydrocarbon groups, such as methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, and n-pentadecyl groups; branched saturated hydrocarbon groups, such as isopropyl, 2-methylpropyl, and 2-methylbutyl groups; linear unsaturated hydrocarbon groups, such as, 2-propenyl, 2-propynyl, and (2E)-2-hexenyl groups; branched unsaturated hydrocarbon groups, such as 2-methyl-2-propenyl group; cyclic saturated hydrocarbon groups, such as cyclopropyl, 2-methylcyclopropyl, cyclobutyl, and cyclopentyl groups; and isomers thereof. A part of the hydrogen atoms in these hydrocarbon groups may be substituted with, e.g., a methyl or ethyl group.

As the monovalent hydrocarbon groups $R^2$ and $R^3$, methyl, ethyl, n-butyl, 2-methylpropyl, 2-methylbutyl and (2E)-2-hexenyl groups are preferable in view of the handling and the chemical structure of the sex pheromones.

Alternatively, $R^2$ and $R^3$ may together form a divalent hydrocarbon group having 2-10 carbon atoms, preferably 2-6 carbon atoms, more preferably 2-4 carbon atoms, $R^2$-$R^3$.

Non-limiting examples of the divalent hydrocarbon group $R^2$-$R^3$ include linear saturated hydrocarbon groups, such as ethylene, 1,3-propylene, and 1,4-butylene groups; branched saturated hydrocarbon groups, such as 1,2-propylene, 2,2-dimethyl-1,3-propylene, 1,2-butylene, 1,3-butylene, and 2,3-butylene groups; linear unsaturated hydrocarbon groups, such as 1-vinylethylene, and (Z)-2-butene-1,4-diyl groups; branched unsaturated hydrocarbon groups, such as 2-methylene-1,3-propylene group; cyclic hydrocarbon groups, such as 1,2-cyclopropylene, 1,2-cyclobutylene, 1,2-cyclopentylene, 1,2-cyclohexylene, and 1,2-phenylene groups; and isomers thereof. A part of the hydrogen atoms in these hydrocarbon groups may be substituted with, e.g., a methyl or ethyl group.

In view of the reactivity in the deprotection, and for easier purification and availability, the divalent hydrocarbon group, $R^2$-$R^3$, is preferably a lower (preferably C2-C4) hydrocarbon group which is highly reactive, and whose byproducts formed by the deprotection can be easily removed by evaporation or washing with water. In view of the above, especially preferable examples of the divalent hydrocarbon group $R^2$-$R^3$ include ethylene, 1,2-propylene, 1,3-propylene, 1,2-butylene, 1,3-butylene, and 2,3-dimethyl-2,3-butylene groups.

For the production of sex pheromone, preferable examples of the 9,9-dialkoxy-7-nonynoate ester (1) include methyl 9,9-dimethoxy-7-nonynoate, ethyl 9,9-dimethoxy-7-nonynoate, butyl 9,9-dimethoxy-7-nonynoate, 2-methylpropyl 9,9-dimethoxy-7-nonynoate, 2-methylbutyl 9,9-dimethoxy-7-nonynoate, (2E)-2-hexenyl9,9-dimethoxy-7-nonynoate, methyl 9,9-diethoxy-7-nonynoate, ethyl 9,9-diethoxy-7-nonynoate, butyl 9,9-diethoxy-7-nonynoate, 2-methylpropyl 9,9-diethoxy-7-nonynoate, 2-methylbutyl 9,9-diethoxy-7-nonynoate. (2E)-2-hexenyl 9,9-diethoxy-7-nonynoate, methyl 9,9-dibutoxy-7-nonynoate, ethyl 9,9-dibutoxy-7-nonynoate, butyl9,9-dibutoxy-7-nonynoate, 2-methylpropyl 9,9-dibutoxy-7-nonynoate, 2-methylbutyl 9,9-dibutoxy-7-nonynoate, (2E)-2-hexenyl 9,9-dibutoxy-7-nonynoate, methyl 9,9-bis(2-methylpropoxy)-7-nonynoate, ethyl 9,9-bis(2-methylpropoxy)-7-nonynoate, butyl 9,9-bis(2-methylpropoxy)-7-nonynoate, 2-methylpropyl 9,9-bis(2-methylpropoxy)-7-nonynoate, 2-methylbutyl 9,9-bis(2-methylpropoxy)-7-nonynoate, (2E)-2-hexenyl 9,9-bis(2-methylpropoxy)-7-nonynoate, methyl 9,9-bis(2-methylbutoxy)-7-nonynoate, ethyl 9,9-bis(2-methylbutoxy)-7-nonynoate, butyl 9,9-bis(2-methylbutoxy)-7-nonynoate, 2-methylpropyl 9,9-bis(2-methylbutoxy)-7-nonynoate, 2-methylbutyl 9,9-bis(2-methylbutoxy)-7-nonynoate, (2E)-2-hexenyl 9,9-bis(2-methylbutoxy)-7-nonynoate, methyl 9,9-bis[(2E)-2-hexen-1-yloxy]-7-nonynoate, ethyl 9,9-bis[(2E)-2-hexen-1-yloxy]-7-nonynoate, butyl 9,9-bis[(2E)-2-hexen-1-yloxy]-7-nonynoate, 2-methylpropyl 9,9-bis[(2E)-2-hexen-1-yloxy]-7-nonynoate, 2-methylbutyl9,9-bis[(2E)-2-hexen-1-yloxy]-7-nonynoate, and (2E)-2-hexenyl9,9-bis[(2E)-2-hexen-1-yloxy]-7-nonynoate.

It should be noted that the 9,9-dialkoxy-7-nonynoate ester (1) may be converted into any desirable acetal form via transacetalization or into any desirable ester form via trans-esterification.

Next, a process for preparing the 9,9-dialkoxy-7-nonynoate ester (1) will be described in more detail.

The 7,7-dialkoxy-5-heptynyl malonate diester of the general formula (9) may be prepared by alkylating a 7-halo-1,1-dialkoxy-2-heptyne of the general formula (7) with a malonate diester of the general formula (8) shown below.

The alkylation may be performed by a reaction of a 7-halo-1,1-dialkoxy-2-heptyne (7) with a malonate diester (8) in the presence of a base in a solvent. The groups $R^2$ and $R^3$ in the 7-halo-1,1-dialkoxy-2-heptyne (7) are as described above. The group $R^1$ in the malonate diester (8) is as described above. The groups $R^1$, $R^2$, and $R^3$ in the 7,7-dialkoxy-5-heptynyl malonate diester (9) are as described above.

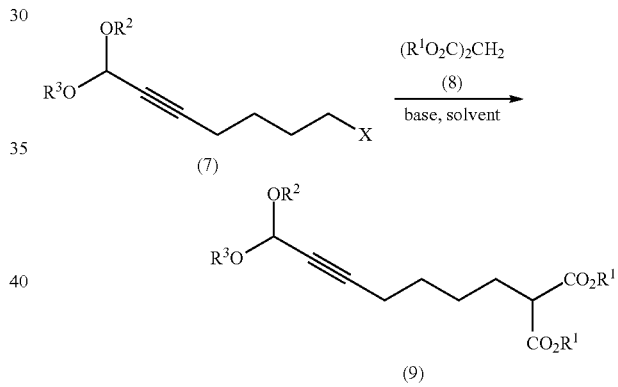

The group X in the 7-halo-1,1-dialkoxy-2-heptyne (7) is a halogen atom, such as chlorine, bromine and iodine atoms. Chlorine and bromine atoms are preferable in view of the reaction selectivity.

Non-limiting examples of the 7-halo-1,1-dialkoxy-2-heptyne (7) include 7-chloro-1,1-dimethoxy-2-heptyne, 7-bromo-1,1-dimethoxy-2-heptyne, 7-iodo-1,1-dimethoxy-2-heptyne, 7-chloro-1,1-diethoxy-2-heptyne, 7-bromo-1,1-diethoxy-2-heptyne, and 7-iodo-1,1-diethoxy-2-heptyne. For the production of sex pheromone, 7-chloro-1,1-dimethoxy-2-heptyne and 7-chloro-1,1-diethoxy-2-heptyne are preferable.

The 7-halo-1,1-dialkoxy-2-heptyne (7) may be prepared, for example, by deprotonating a 6-halo-1-hexyne using a Grignard reagent, followed by a reaction with an orthoformate ester.

The halogen atom in the 6-halo-1-hexyne is as described above for X.

Non-limiting examples of the 6-halo-1-hexyne include 6-chloro-1-hexyne, 6-bromo-1-hexyne, and 6-iodo-1-hexyne. 6-Chloro-1-hexyne is preferable for easier production.

As the Grignard reagent, methylmagnesium chloride, ethylmagnesium chloride, n-propylmagnesium chloride, or n-butylmagnesium chloride may be used.

Non-limiting examples of the orthoformate ester include methyl orthoformate, ethyl orthoformate, butyl orthoformate, 2-methylpropyl orthoformate, 2-methylbutyl orthoformate, and (2E)-2-hexenyl orthoformate. Methyl orthoformate and ethyl orthoformate are preferable in view of economical efficiency.

It should be noted that the 7-halo-1,1-dialkoxy-2-heptyne (7) may be converted into any desirable acetal form by transacetalization.

Non-limiting examples of the malonate diester (8) include dimethyl malonate, diethyl malonate, dipropyl malonate, diisopropyl malonate, dibutyl malonate, bis(2-methylpropyl) malonate, dipentyl malonate, bis(2-methylbutyl) malonate, dihexyl malonate, and bis[(2E)-2-hexenyl) malonate. Dimethyl malonate and diethyl malonate are preferable in view of the cost.

In view of the reaction rate, the malonate diester may be used preferably in an amount of from 1.0 to 2.0 moles per mole of the 7-halo-1,1-dialkoxy-2-heptyne (7).

Non-limiting examples of the base that may be used in the alkylation include carbonates, such as lithium carbonate, sodium carbonate, calcium carbonate, potassium carbonate, cesium carbonate, and barium carbonate; hydrides, such as sodium hydride, potassium hydride, and calcium hydride; alkoxides, such as lithium methoxide, lithium ethoxide, lithium tert-butoxide, lithium tert-amyloxide, sodium methoxide, sodium ethoxide, sodium tert-butoxide, sodium tert-amyloxide, potassium methoxide, potassium ethoxide, potassium tert-butoxide, and potassium tert-amyloxide; and metal amides, such as lithium amide, lithium diisopropylamide, lithium hexamethyldisilazide, lithium dicyclohexylamide, sodium amide, sodium hexamethyldisilazide, and potassium hexamethyldisilazide. In order to efficiently produce the desired 7,7-dialkoxy-5-heptynyl malonate diester (9) while inhibiting dialkylation, carbonate salts, such as lithium carbonate, sodium carbonate, calcium carbonate, potassium carbonate, cesium carbonate, barium carbonate are preferably used as the base in the alkylation. These bases may be used alone or in combination.

The base may be used preferably in an amount of from 0.5 to 2.5 moles per mole of the 7-halo-1,1-dialkoxy-2-heptyne (7) in view of the reactivity.

Optionally, a halide may be further used in the alkylation in order to enhance the reaction rate. Non-limiting examples of the halides include alkali metal halides, such as alkali metal bromides, e.g., lithium bromide, sodium bromide, potassium bromide; and alkali metal iodides, e.g., lithium iodide, sodium iodide, potassium iodide. Alkali metal iodides, such as lithium iodide, sodium iodide, and potassium iodide, are preferable in view of the reactivity. These halides may be used alone or in combination.

In view of the reactivity, the halide may be used preferably in an amount of from 0.001 to 2 moles per mole of the 7-halo-1,1-dialkoxy-2-heptyne (7).

Non-limiting examples of the solvent that may be used in the alkylation include polar solvents, such as N,N-dimethylformamide, N,N-dimethylacetamide, dimethyl sulfoxide, and acetonitrile; hydrocarbon solvents, such as toluene, and hexane; and ether solvents, such as tetrahydrofuran, 4-methyltetrahydropyran, and diethyl ether. N,N-Dimethylacetamide is preferable in view of the reactivity. These solvents may be used alone or in combination.

In view of the reactivity, the solvent may be used preferably in an amount of from 300 to 2,000 grams per mole of the 7-halo-1,1-dialkoxy-2-heptyne (7).

The temperature of the alkylation may vary depending on the type of the solvent to be used. It ranges preferably from 35° C. to 189° C. in view of the reactivity.

The duration of the alkylation may vary depending on the type of the solvent to be used. It ranges preferably from 3 to 30 hours for completion of the reaction.

For the production of the sex pheromones, preferable examples of the 7,7-dialkoxy-5-heptynyl malonate diester (9) include 7,7-dimethoxy-5-heptynyldimethyl malonate, 7,7-dimethoxy-5-heptynyldiethyl malonate, 7,7-dimethoxy-5-heptynyldibutyl malonate, 7,7-dimethoxy-5-heptynylbis(2-methylpropyl) malonate, 7,7-dimethoxy-5-heptynylbis(2-methylbutyl) malonate, 7,7-dimethoxy-5-heptynylbis[(2E)-2-hexenyl) malonate, 7,7-diethoxy-5-heptynyldimethyl malonate, 7,7-diethoxy-5-heptynyldiethyl malonate, 7,7-diethoxy-5-heptynyldibutyl malonate, 7,7-diethoxy-5-heptynylbis(2-methylpropyl) malonate, 7,7-diethoxy-5-heptynylbis(2-methylbutyl) malonate, and 7,7-diethoxy-5-heptynylbis[(2E)-2-hexenyl) malonate.

It should be noted that the 7,7-dialkoxy-5-heptynyl malonate diester (9) may be converted into any desirable acetal form via transacetalization or into any desirable ester form via transesterification.

9,9-Dialkoxy-7-nonynoate ester (1) may be prepared by the Krapcho reaction of the 7,7-dialkoxy-5-heptynyl malonate diester of the general formula (9).

The Krapcho reaction may be carried out by heating the 7,7-dialkoxy-5-heptynyl malonate diester (9) in the presence of a salt in a solvent.

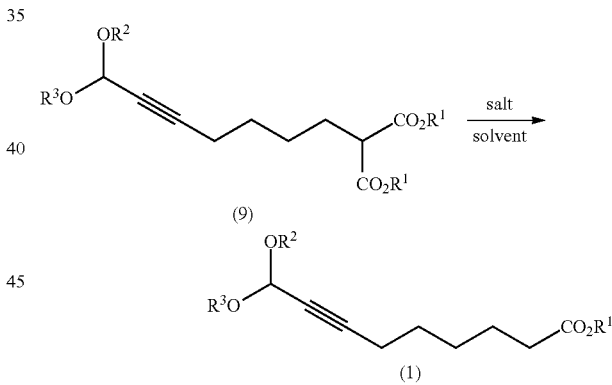

Non-limiting examples of the salt that may be used in the Krapcho reaction include lithium salts, such as lithium chloride, lithium bromide, lithium iodide, and lithium carbonate; sodium salts, such as sodium fluoride, sodium chloride, sodium bromide, sodium iodide, sodium cyanide, sodium acetate, sodium nitrate, sodium dihydrogen phosphate, sodium phosphate, disodium hydrogen phosphate, sodium carbonate, sodium sulfate, and sodium hydrogen sulfate; potassium salts, such as potassium chloride, potassium bromide, potassium iodide, potassium cyanide, potassium acetate, potassium nitrate, potassium dihydrogen phosphate, potassium phosphate, dipotassium hydrogen phosphate, potassium carbonate, potassium sulfate, and potassium hydrogen sulfate; magnesium salts, such as magnesium chloride; calcium salts, such as calcium carbonate; cesium salts such as cesium carbonate; and barium salts, such as barium carbonate. Alkali metal iodides, such as sodium iodide, and potassium iodide, or alkali metal carbonates, such as sodium carbonate, potassium carbonate, and cesium carbonate are preferable in view of the reactivity. These salts may be used alone or in combination.

In view of the reactivity, the salt may be used preferably in an amount of from 1.0 to 5.0 moles per mole of the 7,7-dialkoxy-5-heptynyl malonate diester (9).

Non-limiting examples of the solvent that may be used in the Krapcho reaction include polar solvents, such as N,N-dimethylformamide, N,N-dimethylacetamide, dimethyl sulfoxide, and acetonitrile; hydrocarbon solvents, such as toluene, and hexane; and ether solvents, such as tetrahydrofuran, 4-methyltetrahydropyran, and diethyl ether. N,N-Dimethylacetamide is preferable in view of the reactivity.

In view of the reactivity, the salt may be used preferably in an amount of from 300 to 2,000 grams per mole of the 7,7-dialkoxy-5-heptynyl malonate diester (9).

Optionally, water may be further used in order to enhance the reaction rate.

In view of the reactivity, water may be used preferably in an amount of 1.0 to 5.0 moles per mole of the 7,7-dialkoxy-5-heptynyl malonate diester (9).

The temperature of the Krapcho reaction may vary depending on the type of the solvent to be used. It ranges preferably from 100° C. to 190° C. in view of the reactivity.

The duration of the Krapcho reaction may vary depending on the type of the solvent to be used. It ranges preferably from 5 to 100 hours for completion of the reaction.

The alkylation step and the Krapcho reaction step may be carried out separately so that the Krapcho reaction is conducted after the isolation of the 7,7-dialkoxy-5-heptynyl malonate diester (9) produced by the alkylation. However, the Krapcho reaction step is preferably carried out in situ in a successive manner after the alkylation step (hereinafter called "one-pot" reactions). Such successive reactions save time needed for work-up, concentration and recharging. Further, the solvent used in the alkylation step can be used successively in the Krapcho reaction, and a salt formed as a byproduct in the alkylation step can be used in the Krapcho reaction. Thus, one can save reagents required and reduce the amount of waste, and therefore reduce the environmental burden.

In the case of one-pot reactions, it is preferable to use a carbonate salt as the base, such as lithium carbonate, sodium carbonate, calcium carbonate, potassium carbonate, cesium carbonate, or barium carbonate, because these work also as the salt in the Krapcho reaction.

The base may be used preferably in an amount of from 1.0 to 2.5 moles per mole of the 7-halo-1,1-dialkoxy-2-heptyne (7) in order to inhibit the dialkylation and to allow the Krapcho reaction to proceed efficiently.

Also, in the case of one-pot reactions, water may be further used in the Krapcho reaction in order to enhance the reaction rate.

Water may be used preferably in an amount of from 1.0 to 2.5 moles per mole of the 7-halo-1,1-dialkoxy-2-heptyne (7) in view of the reactivity.

A halide and its amount and a solvent and its amount in the one-pot reactions may be similar as those in the alkylation.

In the case of one-pot reactions, the temperature and duration of the alkylation and those of the Krapcho reaction are as already described above.

Next, a process for preparing a (7E)-7,9-decadienoate ester will be described in more detail.

A 9,9-dialkoxy-7-nonenoate ester of the general formula (2) may be prepared by reducing the 9,9-dialkoxy-7-nonynoate ester (1) as shown below. In the formula (2) for the 9,9-dialkoxy-7-nonenoate ester, $R^1$, $R^2$ and $R^3$ are as already described above.

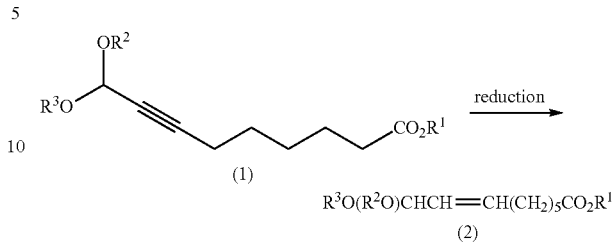

The reduction may be a catalytic hydrogenation; a reduction using potassium hydroxide and N,N-dimethylformamide (DMF) in the presence of a palladium catalyst such as palladium acetate; a reduction using zinc in an alcohol solvent; a Birch reduction; a reduction via hydrosilylation to form a vinylsilane, followed by desilylation; and a reduction via hydroboration with a dialkylborane, followed by protonation. In view of the selectivity and productivity, a catalytic hydrogenation, a reduction using potassium hydroxide and N,N-dimethylformamide (DMF) in the presence of a palladium catalyst such as palladium acetate, and a reduction using zinc in an alcohol solvent are preferable, with the catalytic hydrogenation being more preferable.

The catalytic hydrogenation may be carried out by introducing a hydrogen gas in the presence of a metal catalyst.

Non-limiting examples of the metal catalyst that may be used in the catalytic hydrogenation include Lindlar catalyst; palladium catalysts, such as a palladium-carbon catalyst, and a Pd-PEI catalyst which comprises palladium-carbon poisoned with a polyethyleneimine polymer (PEI); nickel catalysts, such as nickel boride catalysts and P-2 nickel boride catalyst (Thomas J. Caggiano et al. Encyclopedia of Reagents for Organic Synthesis: 3694-3699) (hereinafter called also "P-2Ni catalyst"); and platinum catalysts, such as Adams' catalyst. In view of the economical efficiency, the Lindlar catalyst and nickel catalysts are preferable.

The amount of the metal catalyst may differ depending on the type of catalyst. A solid catalyst, such as the Lindlar catalyst, is used preferably in an amount of from 0.01 to 50.00 grams per mole of the 9,9-dialkoxy-7-nonynoate ester (1) in view of the reactivity. A P-2Ni catalyst is preferably used in an amount of from 0.001 to 0.50 mole calculated as the nickel compound per mole of the 9,9-dialkoxy-7-nonynoate ester (1).

It should be noted that a solid catalyst may be dispersed in a solvent.

When the activity of the metal catalyst is too high, a catalyst poison may be used as needed.

Non-limiting examples of the catalyst poison that may be used in the catalytic hydrogenation include amine compounds, such as pyridine, quinoline, and ethylenediamine; and sulfur compounds, such as benzenethiol, diphenyl sulfide, dimethyl sulfide, and dimethyl sulfoxide.

The amount of the catalyst poison may vary depending on the type of catalyst poison. This ranges preferably from 0.0001 to 10.000 grams per mole of the 9,9-dialkoxy-7-nonynoate ester (1) in view of the reaction rate and the geometric selectivity.

Non-limiting examples of the solvent that may be used in the catalytic hydrogenation include polar solvents, such as acetonitrile, ethyl acetate, and methyl acetate; hydrocarbon solvents, such as toluene, pentane, hexane, heptane, cyclohexane, and cyclohexene; and alcohol solvents, such as methanol, ethanol, propanol, butanol, pentanol, hexanol, 2-propanol, 2-butanol, and cyclohexanol. These solvents may be used alone or in combination.

In view of the reactivity in the catalytic hydrogenation, an alcohol solvent, such as methanol, ethanol, propanol, butanol and 2-propanol, is preferably used in the case of a nickel catalyst; a hydrocarbon solvent such as hexane in the case of the Lindlar catalyst; a polar solvent, such as methyl acetate and ethyl acetate, in the case of a palladium catalyst, such as palladium carbon.

The amount of the solvent to be used may vary depending on the types of the catalyst and solvent to be used. It ranges preferably from 0 to 1,000 grams per mole of the 9,9-dialkoxy-7-nonynoate ester (1) in view of the reactivity.

The temperature for the catalytic hydrogenation may vary depending on the types of the catalyst and solvent to be used. It ranges preferably from 40° C. to 160° C. in view of the geometrical selectivity.

The duration of the catalytic hydrogenation ranges preferably from 1 to 50 hours in view of the yield.

The reduction using potassium hydroxide and N,N-dimethylformamide (DMF) in the presence of a palladium catalyst such as palladium acetate may be carried out preferably at a temperature in the range of from 100° C. to 180° C. for a period of from 6 to 20 hours.

The reduction using zinc may be carried out in an alcohol solvent.

Alcohols that may be used as the solvent preferably have 1 to 10 carbon atoms, more preferably 1 to 5 carbon atoms. Non-limiting examples of the alcohols for use as the solvent include linear alcohols, such as methanol, ethanol, propanol, butanol, pentanol, hexanol, heptanol, octanol, nonanol, and decanol; branched alcohols, such as 2-propanol and 2-butanol; and cyclic alcohols such as cyclohexanol. In view of the reactivity, alcohols having 1 to 5 carbon atoms, such as methanol, ethanol, propanol, butanol, pentanol, and 2-propanol, are preferable. The alcohol may be used preferably in an amount of from 46 to 1,000 grams per mole of the 9,9-dialkoxy-7-nonynoate ester (1) in view of the reactivity.

As used herein, the term "zinc" is intended to mean metal zinc or activated zinc as hereinafter described in more detail. The amount of zinc to be used ranges preferably from 1.0 to 20.0 moles per mole of the 9,9-dialkoxy-7-nonynoate ester (1), in view of the reactivity.

The reduction using zinc in the alcohol solvent may require a prolonged reaction time due to a low reactivity of zinc. If necessary, an activator for zinc may be added, or activated zinc ready-made may be used.

Non-limiting examples of the activator include 1,2-dibromoethane, cuprous chloride, cuprous bromide, cuprous iodide, lithium bromide, iodine, and chlorotrimethylsilane. These activators may be used alone or in combination. The activator may be used preferably in an amount of from 0.01 to 10.0 moles per mole of the 9,9-dialkoxy-7-nonynoate ester (1), in view of the reactivity.

The activated zinc may be prepared, e.g., by treating metal zinc with an acid such as hydrochloric acid, or by reducing zinc chloride with metal lithium in tetrahydrofuran.

The reduction using zinc in an alcohol solvent may be preferably carried out at a temperature in the range of from 0° C. to 100° C. for a period of from 1 to 12 hours.

The Birch reduction may be preferably carried out at a temperature in the range of from −40° C. to 0° C. for a period of from 1 to 10 hours.

In the reduction via hydrosilylation to form a vinylsilane, followed by desilylation, the hydrosilylation may be carried out with a trialkylsilane using a metal catalyst, such as Wilkinson catalyst or Trost catalyst.

The hydrosilylation may be preferably carried out at a temperature in the range of from 5° C. to 100° C. for a period of 2 to 12 hours.

The desilylation after the hydrosilylation may be preferably carried out using an acid, such as hydrogen iodide, acetyl chloride, sulfuric acid, and hydrochloric acid, or titanium tetrachloride or iodine at a temperature in the range of from 5° C. to 80° C. for a period of 1 to 8 hours.

In the reduction via hydroboration with a dialkylborane, followed by protonation, the dialkylborane that may be used for the hydroboration preferably has 4 to 12 carbon atoms, more preferably 6 to 12 carbon atoms. Non-limiting examples of the dialkylborane include dicyclohexylborane, disiamylborane, and 9-borabicyclo[3.3.1]nonane (9-BBN).

The hydroboration may be carried out preferably at a temperature in the range of from −20° C. to 20° C. for a period of 3 to 12 hours.

The protonation subsequent to the hydroboration may be carried out using a carboxylic acid, such as acetic acid, trifluoroacetic acid, chloroacetic acid, formic acid, and oxalic acid; a sulfonic acid, such as benzene sulfonic acid or p-toluene sulfonic acid; or a mineral acid, such as sulfuric acid, hydrochloric acid, nitric acid, or phosphoric acid, with a carboxylic acid such as acetic acid being preferable in view of the reactivity.

The protonation may be carried out preferably at a temperature in the range of from 0° C. to 150° C. for a period of 1 to 12 hours.

9,9-Dialkoxy-7-nonenoate esters (2) have geometrical isomers such as (7E)-9,9-dialkoxy-7-nonenoate ester and (7Z)-9,9-dialkoxy-7-nonenoate ester.

For the production of the sex pheromones, preferable examples of the 9,9-dialkoxy-7-nonenoate ester (2) include methyl (7E)-9,9-diethoxy-7-nonenoate, ethyl (7E)-9,9-diethoxy-7-nonenoate, butyl (7E)-9,9-diethoxy-7-nonenoate, 2-methylpropyl (7E)-9,9-diethoxy-7-nonenoate, 2-methylbutyl (7E)-9,9-diethoxy-7-nonenoate, (2E)-2-hexenyl (7E)-9,9-diethoxy-7-nonenoate, methyl (7Z)-9,9-diethoxy-7-nonenoate, ethyl (7Z)-9,9-diethoxy-7-nonenoate, butyl (7Z)-9,9-diethoxy-7-nonenoate, 2-methylpropyl (7Z)-9,9-diethoxy-7-nonenoate, 2-methylbutyl (7Z)-9,9-diethoxy-7-nonenoate, and (2E)-2-hexenyl (7Z)-9,9-diethoxy-7-nonenoate.

The reduction may be carried out so as to selectively give one of the geometrical isomers, or it may be carried out to give a mixture of the geometrical isomers, because the (7E)-9-oxo-7-nonenoate ester isomer (3) can be produced in a convergent manner by the subsequent hydrolysis described below.

It should be noted that the 9,9-dialkoxy-7-nonenoate ester (2) may be converted into any desirable acetal form via transacetalization or into any desirable ester form via transesterification.

The (7E)-9-oxo-7-nonenoate ester of the general formula (3) may be prepared by hydrolysis of the 9,9-dialkoxy-7-nonenoate ester (2). In the formula (3) for the (7E)-9-oxo-7-nonenoate ester (3), $R^1$ is as described above.

$$R^3O(R^2O)CHCH=CH(CH_2)_5CO_2R^1 \xrightarrow[\text{solvent}]{\text{acid, water}}$$
$$(2)$$

$$OHC\diagup\!\!\!\diagdown\!\!\!\diagup\!\!\!\diagdown\!\!\!\diagup\!\!\!\diagdown CO_2R^1$$
$$(3)$$

Non-limiting examples of the acid that may be used in the hydrolysis include inorganic acids, such as hydrochloric acid, and hydrobromic acid; p-toluene sulfonic acid, trifluoroacetic acid, acetic acid, formic acid, oxalic acid, iodotrimethylsilane, and titanium tetrachloride, with hydrochloric acid being preferable in view of the reactivity.

In view of the reactivity, the acid may be used preferably in an amount of from 0.01 to 10.00 moles per mole of 9,9-dialkoxy-7-nonenoate ester (2).

Non-limiting examples of the solvent that may be used in the hydrolysis include hydrocarbon solvents, such as toluene, xylene and hexane; ether solvents, such as tetrahydrofuran, 4-methyltetrahydropyran, and diethyl ether; polar solvents, such as N,N-dimethylformamide, N,N-dimethylacetamide, acetonitrile, dichloromethane, and chloroform; and alcohol solvents, such as methanol and ethanol. These solvents may be used alone or in combination.

An optimal solvent may vary depending on the type of the acid to be used. For example, when oxalic acid is used as the acid, tetrahydrofuran is preferably used as the solvent in view of the reactivity. When hydrochloric acid is used as the acid, it is preferable that no solvent is used or a hydrocarbon solvent such as hexane is used.

In view of the reactivity, the solvent may be used preferably in an amount of from 0 to 3,000 grams per mole of the 9,9-dialkoxy-7-nonenoate ester (2).

In view of the reactivity, water may be used preferably in an amount of from 18 to 3,000 grams per mole of the 9,9-dialkoxy-7-nonenoate ester (2).

The temperature for the hydrolysis may vary depending on the type of the solvent to be used. It ranges preferably from 5° C. to 150° C.

The duration of the catalytic hydrogenation may vary depending on the type of the solvent or a scale of the reaction system. It typically ranges from 1 to 10 hours.

In order to selectively produce a (7E)-9-oxo-7-nonenoate ester (3) in a high geometrical purity through sufficient isomerization, the aqueous solution in the hydrolytic reaction system preferably has a pH of up to 1.0, more preferably a pH in the range of −1.0 to +1.0. The pH value is determined, for example, using a pH indicator paper, or with a pH meter at a temperature of 25° C. of a liquid object.

For the production of the sex pheromones, preferable examples of the (7E)-9-oxo-7-nonenoate ester (3) include methyl (7E)-9-oxo-7-nonenoate, ethyl (7E)-9-oxo-7-nonenoate, butyl (7E)-9-oxo-7-nonenoate, 2-methylpropyl (7E)-9-oxo-7-nonenoate, 2-methylbutyl (7E)-9-oxo-7-nonenoate, and (2E)-2-hexenyl (7E)-9-oxo-7-nonenoate.

It should be noted that the (7E)-9-oxo-7-nonenoate ester (3) may be converted into any desirable ester form via transesterification.

A (7E)-7,9-decadienoate ester of the general formula (5) may be prepared by subjecting the (7E)-9-oxo-7-nonenoic acid ester (3) to a Wittig reaction with a triarylphosphonium methylide of the general formula (4). In the formula (5) for the (7E)-7,9-decadienoate ester, $R^1$ is as described above.

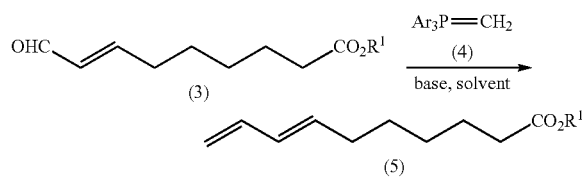

In the formula (4) for the triarylphosphonium methylide, Ar denotes an aryl group having 6 or 7 carbon atoms.

Examples of the aryl groups include phenyl and tolyl groups, with a phenyl group being preferable in view of the easier synthesis.

Non-limiting examples of the triarylphosphonium methylide (4) that may be used in the Wittig reaction include triphenylphosphonium methylide, and tritolylphosphonium methylide, with triphenylphosphonium methylide being preferable in view of economical efficiency.

The triarylphosphonium methylide (4) may be prepared by a reaction of a methyltriarylphosphonium halide with a base. Non-limiting examples of the methyltriarylphosphonium halide include methyltriphenylphosphonium chloride, methyltriphenylphosphonium bromide, and methyltriphenylphosphonium iodide. In view of the reactivity, methyltriphenylphosphonium iodide is preferable.

For completion of the reaction, the methyltriarylphosphonium halide may be used preferably in an amount of from 1.0 to 1.8 moles per mole of the (7E)-9-oxo-7-nonenoate ester (3).

Non-limiting examples of the base that may be used in the preparation of the triarylphosphonium methylide (4) include metal alkoxides, such as potassium tert-butoxide, sodium tert-butoxide, potassium methoxide, sodium methoxide, potassium ethoxide, sodium ethoxide; alkyl lithium, such as n-butyl lithium, and tert-butyl lithium; and metal amides, such as lithium diisopropylamide, sodium bis(trimethylsilyl) amide. In view of the reactivity, metal alkoxides such as potassium tert-butoxide, sodium methoxide, and sodium ethoxide are preferable.

In order to suppress formation of byproducts, the base may be used preferably in an amount of from 0.9 to 1.7 moles per mole of the (7E)-9-oxo-7-nonenoate ester (3).

Examples of a solvent that may be used in the preparation of the triarylphosphonium methylide (4) include ether solvents, such as tetrahydrofuran, 4-methyltetrahydropyran, and diethyl ether; hydrocarbon solvents, such as toluene, xylene, and hexane; and polar solvents, such as N,N-dimethylformamide, N,N-dimethylacetamide, acetonitrile, dichloromethane, and chloroform. In view of the reactivity, tetrahydrofuran is preferable. These solvents may be used alone or in combination.

The amount of the solvent to be used may vary depending on a scale of a reaction system. In view of the reaction rate, it ranges preferably from 100 to 3,000 grams per mole of the (7E)-9-oxo-7-nonenoate ester (3).

The temperature in the preparation of the triarylphosphonium methylide (4) may vary depending on the type of the solvent to be used. In view of the reactivity, it lies preferably in the range of from −78° C. to 50° C., more preferably in the range of from −10 C.° to 25° C.

The duration for the preparation of the triarylphosphonium methylide (4) may vary depending on the type of the solvent to be used or a scale of a reaction system. It ranges preferably from 0.1 to 10 hours.

An optimal temperature for the Wittig reaction may vary depending on the type of the solvent to be used. It lies preferably in the range of from −78° C. to 50° C., more preferably in the range of from −10 C.° to 40° C.

The duration of the Wittig reaction may vary depending on a scale of a reaction system. It ranges preferably from 1 to 30 hours.

The type and amount of the solvent that may be used in the Wittig reaction may be similar to or different from those of the solvent used for the preparation of the triarylphosphonium methylide (4).

In view of the chemical structure of the sex pheromones, preferable examples of the (7E)-7,9-decadienoate ester (5) include methyl (7E)-7,9-decadienoate, ethyl (7E)-7,9-decadienoate, butyl (7E)-7,9-decadienoate, 2-methylpropyl (7E)-7,9-decadienoate, 2-methylbutyl (7E)-7,9-decadienoate and (2E)-2-hexenyl (7E)-7,9-decadienoate.

Next, an optional process will be described in more detail for replacing an alcohol-derived moiety of a (7E)-7,9-decadienoate ester (5) with another alcohol-derived moiety as needed.

A (7E)-7,9-decadienoate ester having a different ester structure can be prepared by replacing the alcohol-derived moiety of the (7E)-7,9-decadienoate ester (5) with another one. This enables comprehensive production of (7E)-7,9-decadienoate esters, which are sex pheromone components of the Nettle caterpillar.

Replacement of an alcohol-derived moiety of a (7E)-7,9-decadienoate ester (5) with another alcohol-derived moiety can be effected by an indirect conversion process in which a (7E)-7,9-decadienoate ester (5) is converted into a (7E)-7,9-decadienoic acid or a (7E)-7,9-decadienoic halide, followed by esterification; or by a direct conversion process in which a (7E)-7,9-decadienoate ester (5) is converted into another ester by transesterification. Either one of the conversion processes may be chosen in so far as the desired ester is obtained. However, the direct conversion process, transesterification, is preferable in view of simpleness of the procedure.

A (7E)-7,9-decadienoate ester having a different ester structure can be prepared by transesterification of the (7E)-7,9-decadienoate ester (5). The transesterification may be carried out by subjecting the (7E)-7,9-decadienoate ester (5) to a reaction with an alcohol of the general formula (6) in the presence of a catalyst. The groups $R^4$ in the alcohol (6) and the (7E)-7,9-decadienoate ester (5-2) and $R^1$ in the formula (5) are both a monovalent hydrocarbon group having 1-15 carbon atoms, but are different from each other.

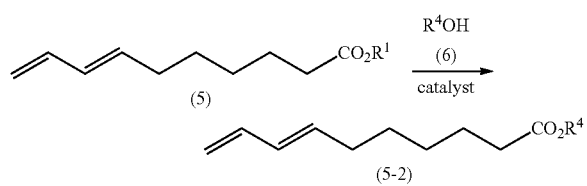

Examples of the catalyst that may be used in the transesterification include metal alkoxides, Lewis acids, acids, and metal carboxylates.

Non-limiting examples of the metal alkoxide include potassium methoxide, sodium methoxide, potassium ethoxide, sodium ethoxide, potassium n-propoxide, sodium n-propoxide, potassium n-butoxide, sodium n-butoxide, potassium tert-butoxide, sodium tert-butoxide, potassium 2-methyl-1-propoxide, sodium 2-methyl-1-propoxide, potassium 2-methyl-1-butoxide, and sodium 2-methyl-1-butoxide.

Non-limiting examples of the Lewis acid include aluminum compounds, zinc compounds, boron compounds, tin compounds, and titanium compounds.

Non-limiting examples of the Lewis acid in the form of an aluminum compound include aluminum acetate, aluminum trichloride, chloroaluminum ethoxide, dichloroaluminum ethoxide, aluminum methoxide, aluminum ethoxide, and aluminum isopropoxide.

Non-limiting examples of the Lewis acid in the form of a zinc compound include zinc acetate, zinc chloride, and zinc bromide.

Non-limiting examples of the Lewis acid in the form of a boron compound include boron trifluoride, boron trichloride, and boron tribromide.

Non-limiting examples of the Lewis acid in the form of a tin compound include tin acetate, tin tetrachloride, dibutyltin dichloride, dibutyltin dimethoxide, dibutyltin oxide, monobutyltin oxide, and dibutyltin dichloride.

Non-limiting examples of the Lewis acid in the form of a titanium compound include titanium tetrachloride, titanium tetrabromide, titanium (IV) methoxide, titanium (IV) ethoxide, titanium (IV) isopropoxide, and titanium (IV) oxide.

Non-limiting examples of the acid include hydrochloric acid, sulfuric acid, trifluoroacetic acid, methanesulfonic acid, benzenesulfonic acid, p-toluene sulfonic acid, Amberlyst 15, chlorotrimethylsilane, chlorotriethylsilane, and tert-butyldimethylchlorosilane.

Non-limiting examples of the metal carboxylate include sodium acetate, potassium acetate, and calcium acetate.

Among these catalysts, metal alkoxides and Lewis acids are preferable in view of the reactivity and less impurities. More preferable are metal alkoxides, such as potassium methoxide, sodium methoxide, potassium ethoxide, sodium ethoxide, potassium tert-butoxide, and sodium tert-butoxide; titanium alkoxides, such as titanium (IV) methoxide, titanium (IV) ethoxide, and titanium (IV) isopropoxide; dibutyltin compounds, such as dibutyltin dimethoxide, dibutyltin oxide, and dibutyltin dichloride; and aluminum alkoxide, such as aluminum methoxide, aluminum ethoxide, and aluminum isopropoxide, and especially preferable are potassium tert-butoxide and titanium (IV) isopropoxide.

The catalyst may be used preferably in an amount of from 0.001 to 2 moles per mole of the alkyl (7E)-7,9-decadienoate (5).

The monovalent hydrocarbon group $R^4$ in the alcohol (6) has 1-15, more preferably 1-10, still more preferably 1-6 carbon atoms.

Non-limiting examples of the monovalent hydrocarbon group $R^4$ include linear alkyl groups, such as methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, and n-pentadecyl groups; branched alkyl groups, such as 1-methylethyl, 2-methylpropyl, 2-methylbutyl, 2-methylpentyl, 2-methylhexyl, 3-methylbutyl, 3-methylpentyl, 3-methylhexyl, 4-methylpentyl, and 4-methylhexyl groups; linear 1-alkenyl groups, such as 1-ethenyl, (1E)-1-propenyl, (1Z)-1-propenyl, (1E)-1-butenyl, and (1Z)-1-butenyl groups; branched 1-alkenyl groups, such as 1-methyl-ethenyl group; linear 2-alkenyl groups, such as 2-propenyl, (2E)-2-butenyl, (2Z)-2-butenyl, (2E)-2-pentenyl, (2Z)-2-pentenyl, (2E)-2-hexenyl, and (2Z)-2-hexenyl groups; branched 2-alkenyl groups, such as 2-methyl-2-propenyl group; linear 3-alkenyl groups, such as 3-butenyl, (3E)-3-pentenyl, (3Z)-3-pentenyl, (3E)-3-hexenyl, and (3Z)-3-hexenyl groups; branched 3-alkenyl groups, such as 3-methyl-3-butenyl group; alkynyl groups, such as 1-propynyl, 3-butynyl, and 1-heptynyl groups; cycloalkyl groups, such as cyclopropyl, 2-methylcyclopropyl, cyclobutyl, cyclopentyl, and cyclohexyl groups; and isomers thereof. A part of the hydrogen atoms in these hydrocarbon groups may be substituted with, e.g., a methyl or ethyl group.

As the monovalent hydrocarbon group $R^4$, methyl, ethyl, n-butyl, 2-methylpropyl, 2-methylbutyl and (2E)-2-hexenyl groups are preferable in view of the handling and for the production of the sex pheromones.

Non-limiting examples of the alcohol (6) include linear saturated alcohols, such as methanol, ethanol, n-propanol, n-butanol, n-pentanol, n-hexanol, n-heptanol, n-octanol, n-nonanol, n-decanol, n-undecanol, n-dodecanol, n-tridecanol, n-tetradecanol, and n-pentadecanol; branched saturated alcohols, such as 1-methyl-1-ethanol, 2-methyl-1-propanol, 2-methyl-1-butanol, 2-methyl-1-pentanol, 2-methyl-1-hexanol, 3-methyl-1-butanol, 3-methyl-1-pentanol, 3-methyl-1-hexanol, 4-methyl-1-pentanol, 4-methyl-1-hexanol; linear 2-alkene-1-ols, such as 2-propen-1-ol, (2E)-2-buten-1-ol, (2Z)-2-buten-1-ol, (2E)-2-penten-1-ol, (2Z)-2-penten-1-ol, (2E)-2-hexen-1-ol, and (2Z)-2-hexen-1-ol; branched 2-alkene-1-ols, such as 2-methyl-2-propen-1-ol; linear 3-alkene-1-ols, such as 3-buten-1-ol, (3E)-3-penten-1-ol, (3Z)-3-penten-1-ol, (3E)-3-hexen-1-ol, and (3Z)-3-hexen-1-ol; branched 3-alkene-1-ols, such as 3-methyl-3-buten-1-ol; linear alkynyl alcohols, such as 1-propyn-1-ol, 3-butyn-1-ol, 1-heptyne-1-ol; and cyclic saturated alcohols, such as cyclopropanol, 2-methylcyclopropanol, cyclobutanol, cyclopentanol, and cyclohexanol.

The amount of the alcohol (6) to be used may vary depending on the type of the catalyst. It ranges preferably from 1.0 to 30.0 moles per mole of the (7E)-7,9-decadienoate ester (5) in view of the reactivity.

Typically, the transesterification may be carried out without solvent. Alternatively, a solvent may be supplementarily used to enhance the removal of an alcohol byproduct derived from the alkyl (7E)-7,9-decadienoate (5).

Any solvent that does not adversely affect the transesterification may be used. For example, a hydrocarbon solvent, such as hexane, toluene, or xylene, or an ether solvent, such as tetrahydrofuran, 4-methyltetrahydropyran, di-n-butyl ether, diethylene glycol dimethyl ether, or diethylene glycol diethyl ether may be preferably used.

There is no particular limitation on the amount of solvent to be used. The solvent may be used preferably in an amount of from 50 to 5,000 grams per mole of the alkyl (7E)-7,9-decadienoate (5) in view of the reactivity.

In a case where an acid or a metal alkoxide is used as the catalyst, an alcohol (6) used as the reactant in the transesterification may also work as the solvent.

When an alcohol (6) used as the reactant in the transesterification is also utilized as the solvent, such an alcohol is used preferably in an amount of from 2 to 1,000 moles per mole of the alkyl (7E)-7,9-decadienoate (5) in view of the reactivity.

The temperature in the transesterification may vary depending on the type of the catalyst to be used. For completion of the reaction, the temperature is preferably above the boiling point of the byproduct alcohol derived from the alkyl (7E)-7,9-decadienoate (5). Alternatively, a lower temperature may be used under an appropriately reduced pressure.

For example, when methyl (7E)-7,9-decadienoate is used as the (7E)-7,9-decadienoate ester (5), the reaction may be carried out at a temperature in the range of from 65° C. to 90° C. at atmospheric pressure, or at a temperature in the range of from 20° C. to 50° C. under reduced pressure of 190 mmHg, so as to efficiently distill off the byproduct methanol.

When ethyl (7E)-7,9-decadienoate is used as the (7E)-7,9-decadienoate ester (5), the reaction may be carried out at a temperature in the range of from 78° C. to 130° C. at atmospheric pressure, or at a temperature in the range of from 20° C. to 70° C. under reduced pressure of 100 mmHg, so as to efficiently distill off the byproduct ethanol.

The duration of the transesterification may vary depending on the type of the catalyst or a scale of the reaction system. It typically ranges from 1 to 30 hours for completion of the reaction.

In view of the chemical structure of the sex pheromones, preferable examples of the (7E)-7,9-decadienoate ester (5-2) include methyl (7E)-7,9-decadienoate, ethyl (7E)-7,9-decadienoate, butyl (7E)-7,9-decadienoate, 2-methylpropyl (7E)-7,9-decadienoate, 2-methylbutyl (7E)-7,9-decadienoate, and (2E)-2-hexenyl (7E)-7,9-decadienoate.

In the manner described above, (7E)-7,9-decadienoate esters which are sex pheromones of the Nettle caterpillar, and 9,9-dialkoxy-7-nonynoate ester (1) which is a useful intermediate, can be prepared.

EXAMPLES

The present invention will be further illustrated by the following Examples, which should not to be construed to limit the scope of the invention.

The term "a crude yield" refers to a yield before purification.

Example 1

Preparation of ethyl 9,9-diethoxy-7-nonynoate (1) $R^1=R^2=R^3=Et$

Potassium carbonate (150.27 g, 1.09 mol), potassium iodide (1.44 g, 0.0087 mol), N,N-dimethylacetamide (608.86 g), diethyl malonate (208.97 g, 1.30 mol) and 7-chloro-1,1-diethoxy-2-heptyne (7) (190.24 g, 0.87 mol) were placed in a reactor at room temperature. The temperature was raised to 130° C., and then the reaction mixture was stirred for 12 hours. Thereafter, water (30.23 g, 1.68 mol) was added while keeping the temperature at 130° C., and the mixture was stirred under reflux conditions at 125° C. for 47.5 hours. After cooled to 40-50° C., the reaction was stopped by adding water (695.84 g) and hexane (173.96 g) to the reaction mixture.

The aqueous layer was removed after phase separation. Water (173.96 g) was added to the organic layer to conduct another phase separation. The organic layer was condensed under reduced pressure to remove hexane, and the residue was subjected to distillation under reduced pressure to obtain ethyl 9,9-diethoxy-7-nonynoate (1) (166.68 g, 0.62 mol) with a yield of 70.9%.

Characterization of ethyl 9,9-diethoxy-7-nonynoate (1) $R^1=R^2=R^3=Et$

[NMR Spectra] $^1$H-NMR (500 MHz, CDCl$_3$): δ1.21 (6H, t, J=7.3 Hz), 1.23 (3H, t, J=7.3 Hz), 1.36-1.44 (2H, m), 1.53 (2H, quint-like, J=7.6 Hz), 1.61 (2H, quint-like, J=7.6 Hz), 2.23 (2H, dt, J=1.6 Hz, 7.6 Hz), 2.27 (2H, t, J=7.3 Hz), 3.51-3.58 (2H, m), 3.67-3.75 (2H, m), 4.10 (2H, q, J=7.3 Hz), 5.22 (1H, t, J=1.6 Hz); $^{13}$C-NMR (125 MHz, CDCl$_3$): δ14.17, 15.03, 18.41, 24.38, 27.89, 28.27, 34.11, 60.15, 60.51, 75.84, 86.02, 91.37, 173.54

[Mass Spectra] EI-Mass Spectra (70 eV): m/z 269 (M$^+$−1), 225, 197, 151, 137, 123, 109, 95, 81, 67, 53

[IR Absorption Spectra] (NaCl): νmax 2977, 2935, 2242, 1736, 1151, 1053

Example 2

Preparation of ethyl (7Z)-9,9-diethoxy-7-nonenoate (2) $R^1=R^2=R^3=Et$

Ethyl 9,9-diethoxy-7-nonynoate (1) (138.45 g, 0.51 mol) and P-2Ni catalyst (17.26 g, 0.0091 mole calculated as a nickel compound) were placed in a reactor, and the temperature was raised to 45-55° C. Then, a hydrogen gas was added to react for 5 hours. After completion of the reaction, the reaction mixture was cooled to 30° C., followed by filtration. Then, water (59 g) was added to wash the reaction mixture. The organic layer was condensed under reduced pressure to remove hexane, and the residue was subjected to distillation under reduced pressure to obtain ethyl (7Z)-9,9-diethoxy-7-nonenoate (2) (134.02 g, 0.49 mol) with a yield of 96.1%.

Characterization of ethyl (7Z)-9,9-diethoxy-7-nonenoate (2) $R^1=R^2=R^3=Et$

[NMR Spectra] $^1$H-NMR (500 MHz, CDCl$_3$): δ1.09 (6H, t, J=7.3 Hz), 1.16 (3H, t, J=7.3 Hz), 1.21-1.36 (4H, m), 1.51 (2H, quint-like, J=7.3 Hz), 2.07 (2H, dq-like, J=1.1 Hz, 7.3 Hz), 2.25 (2H, t, J=7.3 Hz), 3.37-3.44 (2H, m), 3.48-3.56 (2H, m), 4.03 (2H, q, J=7.3 Hz), 5.14 (1H, dd, J=1.1 Hz, 6.7 Hz), 5.35 (1H, ddt, J=11.3 Hz, 1.5 Hz, 6.9 Hz), 5.52 (1H, ddt, J=11.3 Hz, 1.1 Hz, 7.3 HZ); $^{13}$C-NMR (125 MHz, CDCl$_3$): δ14.07, 15.19, 24.24, 27.14, 27.96, 28.43, 33.41, 59.59, 59.78, 97.00, 127.82, 133.51, 172.76

[Mass Spectra] EI-Mass Spectra (70 eV): m/z 271 (M$^+$-1), 227, 181, 153, 135, 57, 43

[IR Absorption Spectra] (NaCl): νmax 2976, 2931, 1737, 1120, 1056

Example 3

Preparation of ethyl (7E)-9-oxo-7-nonenoate (3) $R^1=Et$

Ethyl (7Z)-9,9-diethoxy-7-nonenoate (2) (48.16 g, 0.18 mol), 20 wt % hydrochloric acid (19.07 g, 0.10 mol) and purified water (12.32 g) were placed in a reactor, and stirred at 20-30° C. for 3.5 hours. A pH indicator paper was used to confirm that the water layer had a pH value below 1. Then, hexane (14.32 g) was added. After stirred for 30 minutes, the reaction mixture was allowed to separate into layers. The organic layer was condensed under reduced pressure to obtain ethyl (7E)-9-oxo-7-nonenoate (3) (28.85 g, 0.15 mol, E/Z=99/1) with a crude yield of 82.3%.

Characterization of ethyl (7E)-9-oxo-7-nonenoate (3) $R^1=Et$

[NMR Spectra] $^1$H-NMR (500 MHz, CDCl$_3$): δ1.22 (3H, t, J=7.3 Hz), 1.32-1.40 (2H, m), 1.51 (2H, quint-like, J=7.7 Hz), 1.64 (2H, quint-like, J=7.3 Hz), 2.28 (2H, t, J=7.3 Hz), 2.32 (2H, dq-like, J=1.5 Hz, 7.3 Hz), 4.10 (2H, q, J=7.3 Hz), 6.09 (1H, ddt, J=15.6 Hz, 7.6 Hz, 1.5 Hz), 6.82 (1H, dt, J=15.6 Hz, 6.9 Hz), 9.47 (1H, d, J=7.6 Hz); $^{13}$C-NMR (125 MHz, CDCl$_3$): δ14.16, 24.53, 27.41, 28.50, 32.40, 34.02, 60.19, 133.01, 158.44, 173.49, 194.01

[Mass Spectra] EI-Mass Spectra (70 eV): m/z 199 (M$^+$+1), 180, 152, 124, 111, 83, 70, 55, 41

[IR Absorption Spectra] (NaCl): νmax 2935, 2861, 1733, 1692, 1180, 1125, 977

Example 4

Preparation of ethyl (7E)-7,9-decadienoate (5) $R^1=Et$

Methyltriphenylphosphonium iodide (27.84 g, 0.14 mol) and tetrahydrofuran (150 g) were placed in a reactor, and cooled to −10-0° C. Then, potassium tert-butoxide (18.91 g, 0.17 mol) was added and stirred for 0.5 hour. Then, ethyl (7E)-9-oxo-7-nonenoate (3) (27.84 g, 0.14 mol) was added dropwise over 40 minutes. After completion of the dropwise addition, the reaction mixture was stirred at −10-0° C. for 1.5 hours. Then, the temperature was raised to 20° C., and purified water (83.22 g) was added to the reaction mixture to stop the reaction. After phase separation, the organic layer was condensed under reduced pressure, and the residue was subjected to distillation under reduced pressure to obtain ethyl (7E)-7,9-decadienoate (5) (19.52 g, 0.099 mol, E/Z=99/1) with a yield of 70.8%.

Characterization of ethyl (7E)-7,9-decadienoate (5) $R^1=Et$

[NMR Spectra] $^1$H-NMR (500 MHz, CDCl$_3$): δ1.24 (3H, t, J=7.2 Hz), 1.28-1.36 (2H, m), 1.36-1.44 (2H, m), 1.62 (2H, quint-like, J=7.6 Hz), 2.07 (2H, q-like, J=7.6 Hz), 2.28 (2H, t, J=7.3 Hz), 4.11 (2H, q, J=7.2 Hz), 4.94 (1H, dd, J=10.7 Hz, 1.1 Hz), 5.07 (1H, dd, J=18.3 Hz, 1.1 Hz), 5.67 (1H, dt, J=14.6 Hz, 7.6 Hz), 6.03 (1H, dd, J=15.3 Hz, 10.4 Hz), 6.29 (1H, ddd, J=17.2 Hz, 10.4 Hz, 10.3 Hz); $^{13}$C-NMR (125 MHz, CDCl$_3$): δ14.20, 24.76, 28.59, 28.74, 32.25, 34.23, 60.12, 114.70, 131.03, 135.05, 137.21, 173.72

[Mass Spectra] EI-Mass Spectra (70 eV): m/z 196 (M$^+$), 150, 135, 108, 67, 54, 41

[IR Absorption Spectra] (NaCl): νmax 2932, 2857, 1737, 1179, 1005, 951, 898

Example 5

Preparation of 2-methylpropyl (7E)-7,9-decadienoate (5-2) $R^1$=i-Bu

Ethyl (7E)-7,9-decadienoate (5) (1.84 g, 9.38 mmol) and 2-methyl-1-propanol (6.26 g, 84.41 mmol) were placed in a reactor, and then potassium tert-butoxide (1.05 g, 9.36 mmol) was added at 20-30° C. After stirred for 140 minutes, the mixture was heated to 40° C., and allowed to react for 40 minutes while distilling off ethanol and 2-methyl-1-propanol under reduced pressure of 100 mmHg.

After cooled to 20° C., purified water (30 g) and hexane (30 g) were added to the reaction mixture. After stirred for 30 minutes, the reaction mixture was allowed to separate into layers. The organic layer was condensed under reduced pressure, and the residue was purified by column chromatography to obtain 2-methylpropyl (7E)-7,9-decadienoate (5-2) (1.86 g, 8.27 mmol, E/Z=99/1) with a yield of 88.19%.

Characterization of 2-methylpropyl (7E)-7,9-decadienoate (5-2) $R^1$=i-Bu

[NMR Spectra] $^1$H-NMR (500 MHz, CDCl$_3$): δ0.92 (6H, d, J=6.9 Hz), 1.29-1.37 (2H, m), 1.37-1.44 (2H, m), 1.63 (2H, quint-like, J=7.6 Hz), 1.91 (1H, septet-like, J=6.9 Hz), 2.08 (2H, q-like, J=7.3 Hz), 2.30 (2H, t, J=7.6 Hz), 3.84 (2H, d, J=6.9 Hz), 4.94 (1H, dd, J=10.2 Hz, 1.6 Hz), 5.07 (1H, dd, J=17.0 Hz, 1.5 Hz), 5.68 (1H, dt, J=14.5 Hz, 7.2 Hz), 6.00-6.07 (1H, m), 6.29 (1H, ddd, J=17.1 Hz, 10.3 Hz, 10.0 Hz); $^{13}$C-NMR (125 MHz, CDCl$_3$): δ19.06, 24.84, 27.70, 28.64, 28.76, 32.27, 34.27, 70.35, 114.71, 131.07, 135.06, 137.23, 173.80

[Mass Spectra] EI-Mass Spectra (70 eV): m/z 224 (M$^+$), 150, 121, 108, 41

[IR Absorption Spectra] (NaCl): νmax 2961, 2933, 1737, 1174, 1004, 897

Example 6

Preparation of 2-methylbutyl (7E)-7,9-decadienoate (5-2) $R^1$=2-MeBu

Ethyl (E7)-7,9-decadienoate (5) (1.66 g, 8.45 mmol) and DL-2-methyl-1-butanol (16.54 g, 187.29 mmol) were placed in a reactor, and then potassium tert-butoxide (1.05 g, 9.36 mmol) was added at 20-30° C. After stirred for 220 minutes, the mixture was heated to 40° C., and allowed to react for 2 hours while distilling off ethanol and DL-2-methyl-1-butanol under reduced pressure of 100 mmHg. After cooled to 20° C., purified water (30 g) and hexane (30 g) were added to the reaction mixture. After stirred for 30 minutes, the reaction mixture was allowed to separate into layers. The organic layer was condensed under reduced pressure, and the residue was purified by column chromatography to obtain 2-methylbutyl (7E)-7,9-decadienoate (5-2) (1.86 g, 7.81 mmol, E/Z=99/1) with a yield of 92.5%.

Characterization of 2-methylbutyl (7E)-7,9-decadienoate (5-2) $R^1$=2-MeBu

[NMR Spectra] $^1$H-NMR (500 MHz, CDCl$_3$): δ0.90 (3H, t, J=7.6 Hz), 0.91 (3H, d, J=6.9 Hz), 1.18 (1H, octet-like, J=7.6 Hz), 1.28-1.46 (6H, m), 1.63 (2H, quint-like, J=7.7 Hz), 2.08 (2H, q-like, J=6.9 Hz), 2.30 (2H, t, J=7.7 Hz), 3.90 (2H, dq, J=11.4 Hz, 6.1 Hz), 4.94 (1H, dd, J=9.6 Hz, 1.2 Hz), 5.07 (1H, dd, J=17.0 Hz, 1.5 Hz), 5.68 (1H, dt, 14.6 Hz, 6.9 Hz), 6.00-6.08 (1H, m) 6.29 (1H, ddd, J=16.8 Hz, 10.3 Hz, 10.3 Hz); $^{13}$C-NMR (125 MHz, CDCl$_3$): δ11.18, 16.36, 24.83, 26.00, 28.64, 28.76, 32.27, 34.10, 34.28, 68.87, 114.71, 131.05, 135.06, 137.22, 173.87

[Mass Spectra] EI-Mass Spectra (70 eV): m/z 238 (M$^+$), 150, 121, 108, 71, 55, 43

[IR Absorption Spectra] (NaCl): νmax 2963, 2932, 1737, 1175, 1004, 897

Example 7

Preparation of (2E)-2-hexenyl (7E)-7,9-decadienoate (5-2) $R^1$=(2E)-2-hexenyl Ethyl (7E)-7,9-decadienoate (5) (1.66 g, 8.45 mmol) and (2E)-2-hexen-1-ol (8.91 g, 84.51 mmol) were placed in a reactor, and then potassium tert-butoxide (1.05 g, 9.36 mmol) was added at 20-30° C. After stirred for 150 minutes, the mixture was heated to 65° C., and allowed to react for 40 minutes while distilling off ethanol and trans-2-hexen-1-ol under reduced pressure of 100 mmHg. After cooled to 20° C., purified water (30 g) and hexane (30 g) were added to the reaction mixture. After stirred for 30 minutes, the reaction mixture was allowed to separate into layers. The organic layer was condensed under reduced pressure, and the residue was purified by column chromatography to obtain (2E)-2-hexenyl (7E)-7,9-decadienoate (5-2) (1.93 g, 7.71 mmol, E/Z=99/1) with a yield of 91.2%.

Characterization of (2E)-2-hexenyl (7E)-7,9-decadienoate (5-2) $R^1$=(2E)-2-hexenyl

[NMR Spectra] $^1$H-NMR (500 MHz, CDCl$_3$): λ0.90 (3H, t, J=7.3 Hz), 1.28-1.36 (2H, m), 1.36-1.45 (4H, m), 1.63 (2H, quint-like, J=7.6 Hz). 1.99-2.11 (4H, m), 2.30 (2H, t, J=7.6 Hz), 4.51 (2H, dd, J=6.5 Hz, 1.1 Hz), 4.94 (1H, dd, J=10.1 Hz, 1.5 Hz), 5.08 (1H, dd, J=17.0 Hz, 1.5 Hz), 5.56 (1H, dtt, J=14.2 Hz, 6.5 Hz, 1.5 Hz), 5.68 (1H, dt, J=14.7 Hz, 7.3 Hz), 5.75 (1H, dtt, J=14.3 Hz, 6.5 Hz, 1.2 Hz), 6.03 (1H, ddt, J=15.3 Hz, 10.3 Hz, 0.8 Hz), 6.29 (1H, ddd, J=17.2 Hz, 10.3 Hz, 10.3 Hz); $^{13}$C-NMR (125 MHz, CDCl$_3$): δ13.59, 22.01, 24.76, 28.61, 28.75, 32.27, 34.23, 34.27, 65.06, 114.71, 124.00, 131.04, 135.07, 136.24, 137.22, 173.50.

[Mass Spectra] EI-Mass Spectra (70 eV): m/z 250 (M$^+$), 135, 121, 67, 41

[IR Absorption Spectra] (NaCl): νmax 2958, 2930, 2859, 1737, 1170, 1004, 971, 897

Example 8

Preparation of methyl (7E)-7,9-decadienoate (5-2) $R^1$=Me

Ethyl (7E)-7,9-decadienoate (5) (1.66 g, 8.45 mmol) and methanol (27.06 g, 844.70 mmol) were placed in a reactor, and then potassium tert-butoxide (1.05 g, 9.36 mmol) was added at 20-30° C. After stirred for 190 minutes, the mixture was heated to 40° C., and allowed to react for 30 minutes while distilling off ethanol and methanol under reduced pressure of 100 mmHg. After cooled to 20° C., purified water (30 g) and hexane (30 g) were added to the reaction mixture. After stirred for 30 minutes, the reaction mixture was allowed to separate into layers. The organic layer was condensed under reduced pressure, and the residue was purified by column chromatography to obtain methyl (7E)-7,9-decadienoate (5-2) (1.48 g, 8.13 mmol, E/Z=99/1) with a yield of 96.2%.

Characterization of methyl (7E)-7,9-decadienoate (5-2) $R^1$=Me

[NMR Spectra] 1H-NMR (500 MHz, CDCl3): δ1.28-1.36 (2H, m), 1.36-1.44 (2H, m), 1.62 (2H, quint-like, J=7.6 Hz), 2.07 (2H, q-like, J=6.9 Hz), 2.29 (2H, t, J=7.6 Hz), 3.65 (3H, s), 4.94 (1H, dd, 10.3 Hz, 1.1 Hz), 5.07 (1H, dd, J=17.2 Hz, 1.1 Hz), 5.67 (1H, dt, J=14.5 Hz, 6.9 Hz), 6.03 (1H, ddt, J=10.4 Hz, 15.2 Hz, 0.8 Hz), 6.29 (1H, ddd, J=17.2 Hz, 10.4 Hz, 10.3 Hz); 13C-NMR (125 MHz, CDCl3): δ24.73, 28.60, 28.73, 32.25, 33.96, 51.40, 114.71, 131.06, 135.02, 137.21, 174.14

[Mass Spectra] EI-Mass Spectra (70 eV): m/z 182 (M+), 150, 135, 121, 108, 67, 54, 41

[IR Absorption Spectra] (NaCl): νmax 2932, 1740, 1172, 1005, 899

Example 9

Preparation of butyl (7E)-7,9-decadienoate (5-2) $R^1$=Bu

Ethyl (7E)-7,9-decadienoate (5) (1.66 g, 8.45 mmol), n-butanol (0.75 g, 10.14 mmol) and titanium (IV) isopropoxide (0.024 g, 0.084 mmol) were placed in a reactor, and then heated to 120° C. to distill off ethanol which was formed as a byproduct as the reaction proceeded. After ethanol was completely distilled off, the internal pressure of the reactor was gradually reduced to 1.0 mmHg while raising the internal temperature of the reactor to 140° C., thereby conducing distillation under reduced pressure to obtain butyl (7E)-7,9-decadienoate (5-2) (1.63 g, 7.28 mmol, E/Z=99/1) with a yield of 86.1%.

Characterization of butyl (7E)-7,9-decadienoate
(5-2) $R^1$=Bu

[NMR Spectra] 1H-NMR (500 MHz, CDCl3): δ0.93 (3H, t, J=7.3 Hz), 1.28-1.45 (6H, m), 1.56-1.66 (4H, m), 2.08 (2H, q-like, J=7.2 Hz), 2.28 (2H, t, J=7.3 Hz), 4.06 (2H, t, J=6.5 Hz), 4.94 (1H, dd, J=10.0 Hz, 1.1 Hz), 5.07 (1H, dd, J=17.6 Hz, 1.1 Hz), 5.68 (1H, dt, J=14.7 Hz, 7.2 Hz), 6.03 (1H, ddt, J=15.3 Hz, 10.3 Hz, 0.8 Hz), 6.29 (1H, ddd, J=17.0 Hz, 10.3 Hz, 10.1 Hz); 13C-NMR (125 MHz, CDCl3): δ13.66, 19.10, 24.81, 28.62, 28.75, 30.66, 32.27, 34.26, 64.08, 114.70, 131.05, 135.06, 137.22, 173.82

[Mass Spectra] EI-Mass Spectra (70 eV): m/z 224 (M+), 150, 135, 121, 108, 67, 54, 41

[IR Absorption Spectra] (NaCl): vmax 2959, 2933, 1737, 1176, 1004, 897

The invention claimed is:

1. A method for preparing a (7E)-7,9-decadienoate ester of the general formula (5):

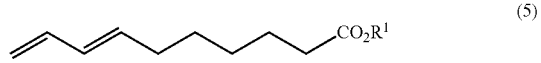
(5)

wherein $R^1$ is a monovalent hydrocarbon group having 1-15 carbon atoms, the method comprising at least steps of:
hydrolyzing a 9,9-dialkoxy-7-nonenoate ester of the general formula (2):

$R^3O(R^2O)CHCH=CH(CH_2)_5CO_2R^1$ (2)

wherein $R^1$ is as defined above, and $R^2$ and $R^3$ are each independently a monovalent hydrocarbon group having 1-15 carbon atoms or together form a divalent hydrocarbon group having 2-10 carbon atoms, $R^2$-$R^3$,
to form a (7E)-9-oxo-7-nonenoate ester of the general formula (3):

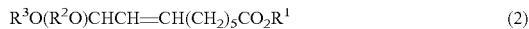
(3)

wherein $R^1$ is as defined above; and
subjecting the (7E)-9-oxo-7-nonenoate ester (3) to a Wittig reaction with a triarylphosphonium methylide of the general formula (4):

$Ar_3P=CH_2$ (4)

wherein Ar is an aryl group having 6 or 7 carbon atoms, to form the (7E)-7,9-decadienoate ester.

2. The method for preparing the (7E)-7,9-decadienoate ester according to claim 1, wherein the method further comprises a step of:
reducing a 9,9-dialkoxy-7-nonynoate ester of the general formula (1):

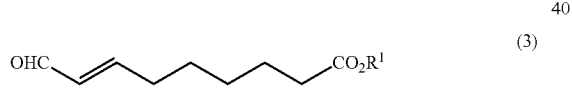
(1)

wherein $R^1$, $R^2$ and $R^3$ are as defined above, to form the 9,9-dialkoxy-7-nonenoate ester (2).

3. The method for preparing the (7E)-7,9-decadienoate ester according to claim 2, wherein the method further comprises a steps of:
alkylating a 7-halo-1,1-dialkoxy-2-heptyne of the general formula (7):

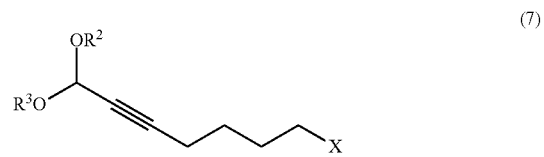
(7)

wherein $R^2$ and $R^3$ are as defined above, and X is a halogen atom,
with a malonate diester of the general formula (8):

$CH_2(COOR^1)_2$ (8)

wherein $R^1$ is as defined above,
to form a 7,7-dialkoxy-5-heptynyl malonate diester of the general formula (9):

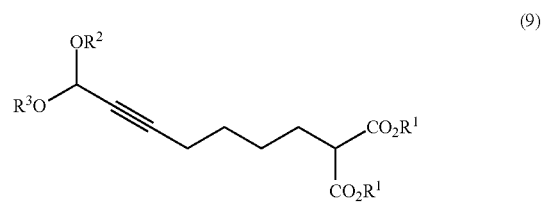
(9)

wherein $R^1$, $R^2$ and $R^3$ are as defined above; and
subjecting the 7,7-dialkoxy-5-heptynyl malonate diester (9) to a Krapcho reaction to form the 9,9-dialkoxy-7-nonynoate ester (1).

4. The method for preparing the (7E)-7,9-decadienoate ester according to claim 3, wherein the Krapcho reaction step is conducted in situ following the alkylation step.

5. The method for preparing a (7E)-7,9-decadienoate ester of the general formula (5-2):

(5-2)

wherein $R^4$ is a monovalent hydrocarbon group having 1-15 carbon atoms and is different from $R^1$ as defined in claim 1,
by transestefication of the (7E)-7,9-decadienoate ester prepared by the method according to claim 1 in the presence of a catalyst with an alcohol of the general formula (6):

$R^4OH$ (6)

wherein $R^4$ is as defined above.

6. A method for preparing a 9,9-dialkoxy-7-nonynoate ester of the general formula (1):

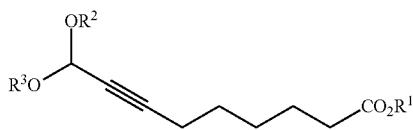
(1)

wherein $R^1$ is a monovalent hydrocarbon group having 1-15 carbon atoms, and $R^2$ and $R^3$ are each independently a monovalent hydrocarbon group having 1-15 carbon atoms or together form a divalent hydrocarbon group having 2-10 carbon atoms, $R^2$-$R^3$, the method comprising at least steps of:
alkylating a 7-halo-1,1-dialkoxy-2-heptyne of the general formula (7):

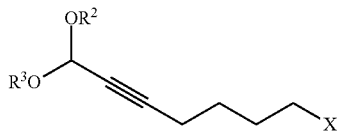
(7)

wherein $R^2$ and $R^3$ are as defined above, and X is a halogen atom,
with a malonate diester of the general formula (8):

 (8)

wherein $R^1$ is as defined above,
to form a 7,7-dialkoxy-5-heptynyl malonate diester of the general formula (9):

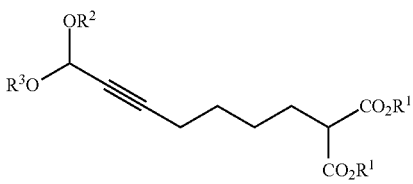
(9)

wherein $R^1$, $R^2$ and $R^3$ are as defined above; and
subjecting the 7,7-dialkoxy-5-heptynyl malonate diester (9) to a Krapcho reaction to form the 9,9-dialkoxy-7-nonynoate ester (1).

7. The method for preparing the 9,9-dialkoxy-7-nonynoate ester according to claim 6, wherein the Krapcho reaction step is conducted in situ following the alkylation step.

8. A 9,9-dialkoxy-7-nonynoate ester of the general formula (1):

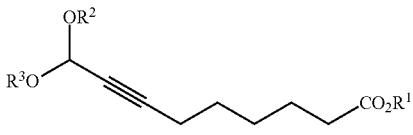
(1)

wherein $R^1$ is a monovalent hydrocarbon group having 1-15 carbon atoms, and $R^2$ and $R^3$ are each independently a monovalent hydrocarbon group having 1-15 carbon atoms or together form a divalent hydrocarbon group having 2-10 carbon atoms, $R^2$-$R^3$.

\* \* \* \* \*